United States Patent [19]

Stephanopoulos et al.

[11] Patent Number: 4,948,728
[45] Date of Patent: Aug. 14, 1990

[54] MONOLITH REACTOR CONTAINING A PLURALITY OF FLOW PASSAGES AND METHOD FOR CARRYING OUT BIOLOGICAL REACTIONS

[75] Inventors: Gregory Stephanopoulos, Winchester, Mass.; Julia A. Kornfield, Menlo Park; Gerald E. Voecks, La Cresenta, both of Calif.

[73] Assignee: California Institute of Technology, Pasadena, Calif.

[21] Appl. No.: 166,258

[22] Filed: Mar. 10, 1988

Related U.S. Application Data

[63] Continuation-in-part of Ser. No. 772,141, Sep. 3, 1985, abandoned.

[51] Int. Cl.$^5$ .................... C12P 1/00; C12N 11/14; C12M 1/40; C12M 1/04
[52] U.S. Cl. ..................... 435/41; 435/174; 435/176; 435/240.23; 435/288; 435/313; 435/813; 435/818
[58] Field of Search ................ 435/41, 174, 176, 182, 435/288, 240.23, 81.8, 813, 313

[56] References Cited

U.S. PATENT DOCUMENTS

| 4,268,423 | 5/1981 | Ruhrbach et al. | 435/176 X |
| 4,440,853 | 4/1984 | Michaels et al. | 435/174 X |
| 4,442,206 | 4/1984 | Michaels et al. | 435/174 X |

FOREIGN PATENT DOCUMENTS 0043382 3/1985 Japan .................................. 435/176

OTHER PUBLICATIONS

Vayenas, et al, Mathematical Modeling of Cross-Flow, Solid-State, Electrochemical Reactors, W. R. Grace & Co., Research Division Columbia, Maryland, 1984, pp. 1–42.
Ghommich, et al., Biotechnology & Bioengineering, vol. XXIV, 1982, pp. 605–617.
Aris, R., Chemical Hydrodyamics, 1983, pp. 815–825.
Matson S. L. Membrane Bioreactors-Trends and Opportunities Paper Presented at Biotech 85 Europe, Geneva, Switzerland, May 21–23, 1985, pp. 1–14.
Benoit, et al., Biotechnology & Bioengineering, vol. XVI, 1975, pp. 1617–1626.

*Primary Examiner*—David M. Naff
*Attorney, Agent, or Firm*—Paul R. Wylie

[57] ABSTRACT

Biological reactions are carried out with a unitary structure, preferably formed of a ceramic material, having a plurality of flow passages including first and second sets of flow passages arranged so that individual passages of the first set are adjacent individual passages of the second set and are separated by walls formed of the ceramic material. The ceramic material is porous to provide mass transfer of gaseous oxygen and biological reaction products while containing liquid in the second set of passages. Walls of the passages may be covered with a gaseous oxygen permeable membrane. Inside walls of the second set of passages may coated with a compound adapted to immobilize biological reaction materials. In a biological reaction, the first set of passages are contacted with a fluid such as an air stream to provide gaseous oxygen, and a fluid flow such as a nutrient medium is established through the second set of flow passages whereby an oxygen flow producing gradient is produced through the porous ceramic material between the first and second sets of flow passages to supply oxygen for cells immobilized on inside walls of the second set of flow passages.

18 Claims, 7 Drawing Sheets

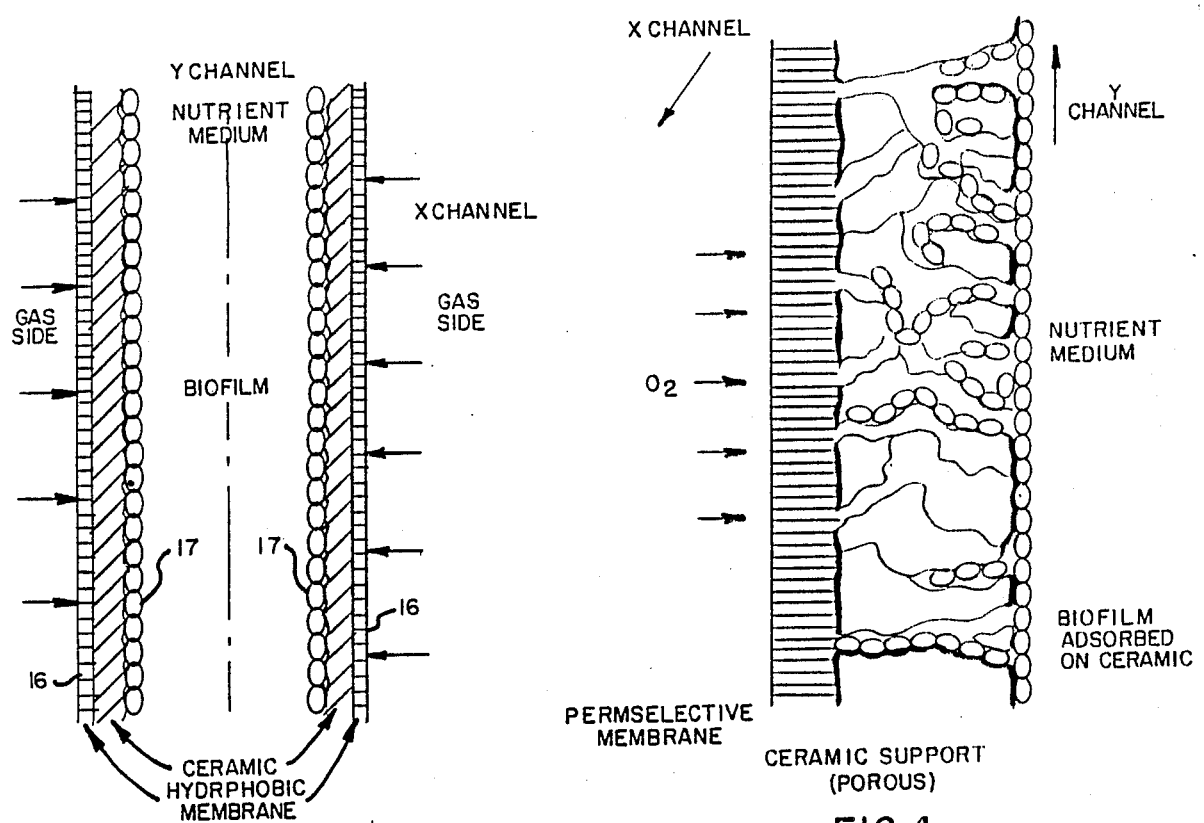
FIG.3
FIG.4
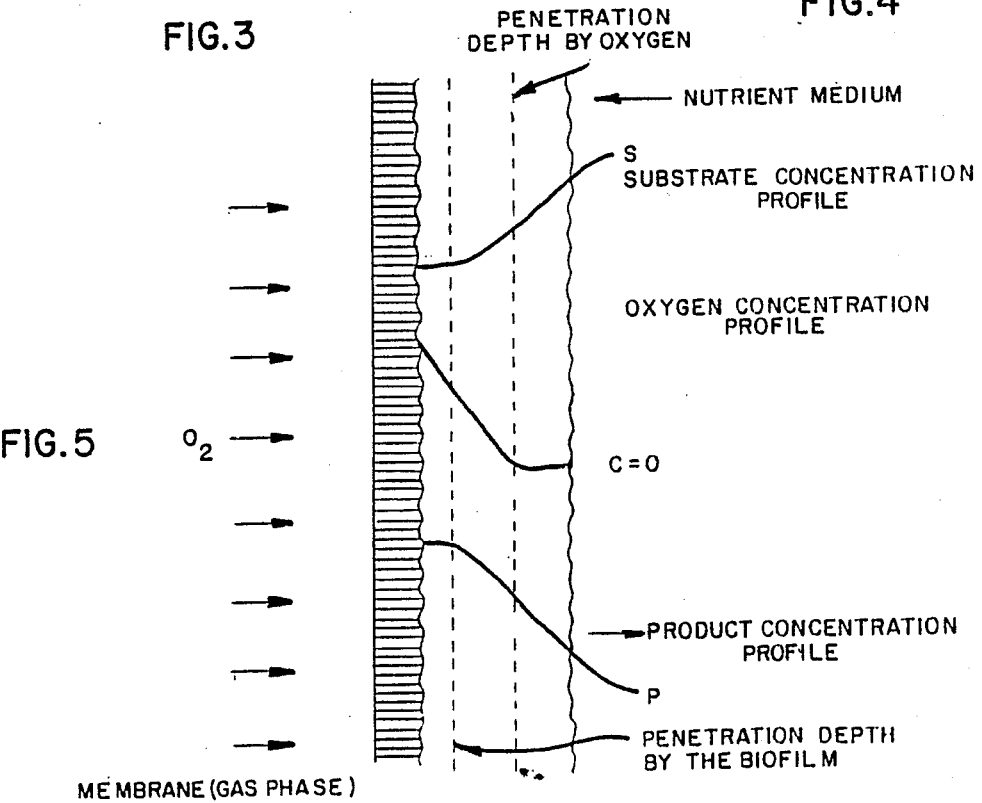
FIG.5

MONOLITH REACTOR CONTAINING A PLURALITY OF FLOW PASSAGES AND METHOD FOR CARRYING OUT BIOLOGICAL REACTIONS

This application is a Continuation-in-Part of application Ser. No. 06/772,141 filed Sept. 3, 1985, now abandoned.

BACKGROUND OF THE INVENTION

This invention relates generally to a method and apparatus for carrying out the transfer of reactants such as oxygen and/or the transfer and separation of products from reactions, which can be biological reactions or the like. Biological reactions using immobilized microorganisms have been the focus of much recent research and development. Notable commercial processes using immobilized cells include glucose isomerization, raffinose hydrolysis and amino acid production. Other useful reactions such as antibiotic modification and organic acid formation and degradation have been extensively studied and some are near the stage of commercial application.

The widespread interest in immobilized cell systems is well justified given the advantages of these systems over freely suspended cells. The most obvious advantage is the continuous use of biomass which is retained in the reactor. The yield with respect to product is thus increased due to the decrease in the amount of biomass synthesis. Cell immobilization also provides the means to make batch processes continuous, and it can be employed with resting cells for continuous secondary metabolite production. The high cell densities achieved by immobilization yield faster reaction rates. Finally, by removing or reducing the cells suspended in the medium, immobilization can improve the rheological properties of the medium while increasing the effective densities of the microorganisms. For these reasons, manyfold productivity increases have been realized with immobilized cell reactors.

There are, to be sure, several problems associated with immobilized cells systems which are due, in general, to the biological system, the immobilization technique, or the reactor system. Immobilization may result in a loss of some of the desirable catalytic activity either because of enzyme inactivation during immobilization, or because of diffusional barriers that decrease substrate access to or product removal from the cells. Packed beds as immobilized cell reactors have the disadvantages of being mass-transfer limited, being subject to plugging, and using only a small fraction of the available cells for biocatalysis. Hollow fiber cell reactors, such as those disclosed in U.S. Pat. No. 4,201,845 to Feder et al, have mass transfer limitations through the membrane that separates the nutrients from the cells.

BRIEF SUMMARY OF THE INVENTION

In accordance with the present invention, there is provided an apparatus and method for carrying out the transfer and separation of fluid reactants and products to and from immobilized cell biological reactions or the like. In the apparatus aspects of the invention, there is provided a unitary structure formed of ceramic or polymeric material having a plurality of flow passages therein which includes first and second sets of flow passages with material communicating means respectively so that different substances can be moved through the respective sets of passage and wherein individual passages of said first set are separated from individual passages of the second set by the material of the unitary structure. This unitary structure (or monolith structure as it is sometimes called) is provided with means for establishing material transfer through the respective sets of passages in a manner such that a biological reaction or the like will take place in the first set of passages with a reactant or a product from the reaction being transferred through the material of the unitary reactor from or to the second set of passages, a flow of said reactant or product having been produced between the passages of said first and second sets respectively.

In the method aspect of the invention, a unitary ceramic structure, or so-called monolith, having the first and second sets of flow passages as outlined above is contacted with a reacting material under conditions giving rise to transfer of reactants and/or products to or form the first set of passages from or the the second set of passages.

In a preferred form of the invention, the reaction can be a biological reaction or a reaction requiring oxygen in said first set of passages.

In a further preferred form of the invention, the first and second sets of passages can be orthogonally positioned to each other.

In an important further preferred form of the invention, a membrane, permeable to the reactants or products to be passed from the individual flow passages of said one set of passages to those of said other set of passages, but impermeable to other materials, is coated on, or covers, the inside walls of either the passages of said first set or the passages of said second set respectively, or is otherwise associated with said walls.

In either the method or apparatus aspects of the invention, immobilized cells can be present on the walls of the individual passages of the second set of passages.

BRIEF DESCRIPTION OF THE DRAWINGS

The invention will be more fully understood with reference to the accompanying drawings showing certain specific embodiments of the invention and an apparatus for the testing thereof wherein:

FIG. 3 is a schematic view of a single flow passage according to the invention shown coated with a membrane;

FIG. 4 is a schematic of a segment of ceramic wall material of a unitary reactor between first and second flow passage shown coated with a membrane;

FIG. 5 is a view similar to FIG. 4 but showing a schematic of oxygen, product and substrate concentration profiles across a membrane coated ceramic wall of a unitary reactor;

DETAILED DESCRIPTION OF THE INVENTION

Figure 1:
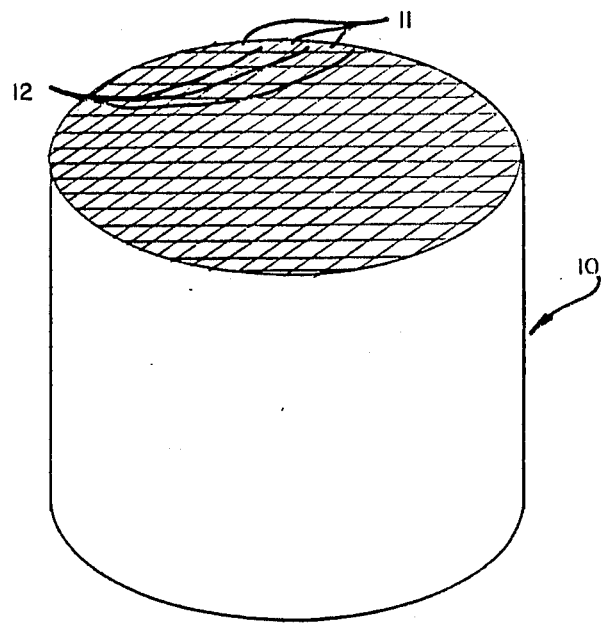
FIG. 1 is a view in perspective of a unitary structure, adapted for use for carrying out biological reactions, according to the invention wherein first and second sets of flow passages are aligned in parallel.

Referring now to FIG. 1 there is a shown a unitary structure, or monolithic reactor as it will sometimes be called herein, formed of ceramic materials. The unitary structure 10 comprises first and second sets of flow passages shown for example as element 11 that are in parallel arrangement to a second set of flow passage 12. Each of the flow passages 11, in this arrangement, is adjacent to a flow passage 12 being mutually separated by a wall of said ceramic material.

Figure 2:
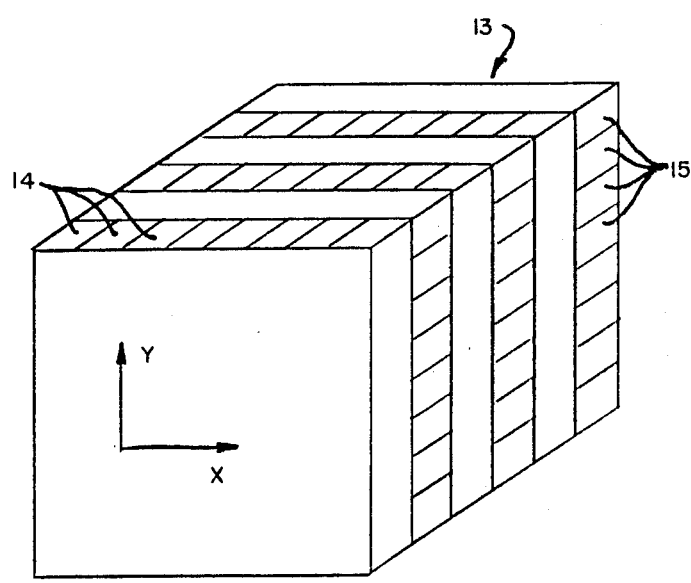
FIG. 2 is a schematic diagram of another form of a unitary reactor according to the invention wherein the first and second sets of flow passages are at right angles.

In FIG. 2 a different arrangement of a monolithic reactor 13 is shown wherein, as shown, schematically, a first set of flow passages 14 and a second set of flow passages 15 are disposed in orthogonal relationship to each other on the respective "X" and "Y" axes.

With regard to the monolithic reactors shown in FIGS. 1 and 2, they are preferably made of ceramic materials by extrusion and firing and can consist of an array of parallel channels as shown in FIG. 1, of square, triangular, hexagonal or sinusoidal geometry. The result, in a preferred form, is a small unit, typically about 6" long by 6" diameter with a high flow surface area. These honeycomb structures constitute unique chemical reactors with high geometric external surface, structural durability, low pressure drop; and uniform flow distribution within the monolith matrix.

High cell loadings can be attained in the structures shown in FIGS. 1 and 2 by adsorption because of the high surface area to volume ratio in the monoliths compared to beads in a packed bed. The required pressure is very low as flow through the flow passages 14 and 15 is unhindered. Cell sloughing in passages 14 or 15 poses no plugging problems since cells can be readily swept from such channels by a flowing stream.

Cross-flow monoliths such as shown in FIG. 2 offer additional advantages over straight-through monoliths as biological catalyst supports. The monolithic reactor 13 consists of two sets of flow passages 14 and 15 respectively, running in perpendicular direction, in alternating layers. Such systems have been explored as reactor-heat exchangers and as solid electrolyte fuel cell reactors but have not heretofore been used as biological reactors. Two separate flow streams are contacted across the walls of the flow channels 14 and 15 of monolith 13 all along its length and width. Because the ceramic material of the monolith is porous, mass transfer is allowed across the walls.

As shown in FIGS. 3 and 4, by applying an appropriately selective permeable membrane 16 to the walls which separate the passages of said first and second sets of flow passages of the reactor, mass transfer between the two segregated streams can be controlled. Selective mass transfer to or from a biofilm 17 offers a new variable which can be used to optimize bioreactor performance and control.

Potential applications of the cross-flow monolithic reactor shown in FIG. 2 include inhibitory product removal, simultaneous reaction and product enrichment, and infusion of limiting substrates into a biofilm.

The material of unitary reactors 10 and 13 must be porous to biological reaction products and generally will have a pore size between 50 angstrom units and 1 millimeter. The porous material must be insoluble in water, nonswellable and structurally sound so that it can form a monolithic reactor 10. The material must be nontoxic to micro-organisms and the surface of the material may have functional groups capable of being modified according to this invention. Inside walls of the second set of flow passages may have a coating of a compound adapted to attach to the ceramic material and to immobilize biological reaction materials.

Materials for the unitary reactors 10 and 13 can be ceramic such as cordierite (made of a alumina, silica and magnesia), steatite (magnesia and silica) and others and additionally such material can be porous glass. The substrate material may also be a polymeric material such as polysulfone. Other ceramic materials well known in the art either slip cast or extruded can also be used. In any event, the substrate material is such that when in combination with a substrate treating compound according to the invention, it will permit passage of selected biological reaction products and/or reactants while preventing passages of unreacted reactants and nonselected by-products of the reaction.

Many useful biological reactions are severely limited by mass transfer of one substrate. In particular, oxygen is the limiting reactant or substrate in numerous whole cell catalyzed processes, including: aceticacid fermentation by *Acetobacter aceti*, antibiotic production by *Pennicillium chrysogenum*, resolution of L-amino acids from racemic mixtures by *Trigonopsis variabilis*, L-glutamic acid production by *Corynebacterium glutamicum*, and others. The cross-flow monolithic reactor as described herein can be used to provide the limiting substrate to cells through a large surface area adjacent to the biofilm. Further, the high surface area and its closeness to the active cells is built into the reactor, rather than being maintained at the expense of high power input and high shear rates as in suspended cultures. Since the pressure drop of flow through the sets of flow passages of the reactor is very small, relatively little power is required to circulate air and medium at sufficiently high rates to achieve good substrate supply, aeration, and product removal.

In accordance with one aspect of this invention, it is demonstrated that a membrane coated porous material can readily be made which retains a liquid stream, uncontaminated, in one set of flow passages, while allowing adequate oxygen supply across the material from a gas stream in another set of flow passages.

Within an immobilized-cell cross-flow monolithic reactor 13, as shown in FIG. 2, the layers of the first set of flow passages 15 running in the X-direction conduct an air stream and the layers of the second set of flow passages 14 running in the orthogonal direction contain a nutrient medium. A hydrophobic, gas-permeable membrane 16 (FIG. 3) is attached or associated with the sides of the flow passages 15 conducting an air stream. The immobilized cells from the nutrients medium form a biofilm on the material of the wall which will penetrate into the pores of the wall from the liquid in flow passages 14 (FIG. 4). For the case of highly aerobic cells, the biofilm can be expected to develop until growth is limited by oxygen or nutrient supply. Therefore, oxygen will be completely consumed, and the concentration of oxygen will go to zero at some point within the ceramic (FIG. 5).

To measure oxygen transfer rates which are realistic for the monolithic reactor configuration of FIGS. 1 and 2, it was necessary to design an experiment which simulates the consumption of oxygen of the ceramic material selected for such unitary or monolithic reactors. The sulfite oxidation system of Cooper, et al, *Ind. and Eng. Chem.*, 36, p 504 (1944), was chosen as the method for measuring oxygen transfer rates. The enhancement of the oxygen transfer rate due to the sulfite reaction is analogous to the enhancement of the oxygen transfer which would occur due to oxygen consumption by a biofilm growing on the ceramic (FIG. 4). The reaction

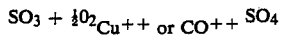

$$r = k_2[O_2]^2$$

$$k_2 = k_2(T, pH, [Co^{++}] \text{ or } [Cu^{++}])$$

can be catalyzed by either copper or cobalt ions. The kinetics of the reaction are second order to oxygen, zero order in sulfite for sulfite concentrations between 0.03 and 1.0N. The rate constant depends on temperature, pH, catalyst and catalyst concentration. The sulfite reaction is easily quantified by idiometric titration which allows quick, reproducible measurement of the oxygen transfer; whereas measurement of oxygen transfer rates using various immobilized cells will require much more time, a more elaborate eperimental apparatus, and oxygen assays tailored to each cell, substrate, and product system. Thus, the sulfite reaction provides an important simplification of the experiments to demonstrate the feasibility of oxygen transfer in th cross-flow monolithic reactor structure of FIG. 2 and to estimate a realistic range of oxygen transfer rates.

Figure 6A:
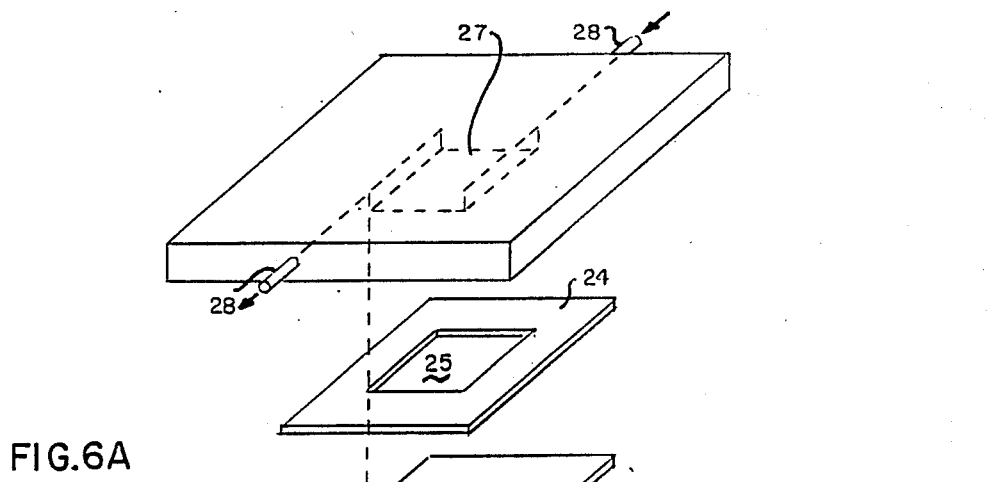
FIGS. 6A and 6B are, respectively, exploded and cross-sectional assembly views of a test cell as described herein.

The other major simplification of the cross-flow monolithic reactor of FIG. 2 for the purpose of facilitating the experiment is to perform the measurements on a single layer. Selectively permeable membranes, such as used as element 16 (FIG. 3), are easily applied to each face of a single layer of flow channels simulating flow channels 14 and 15, forming a sandwich which is easily mounted and sealed into the test cell as shown in FIG. 6A. Due to the repeating structure of the cross-flow monolith, the results of a measurement on a single layer of flow channels may be linearly extrapolated to many layers.

The test cell used for experimentation was designed and built to simulate the conditions in a cross-flow monolith reactor 13 such as shown schematically in FIG. 2.

Corning cordierite monoliths, having a density of 300 channels/in² were used for this study. The 6" by 4" by 4" "race track" monoliths were sliced into slabs 4" by 4" by 3 or 4 layers thick. These slabs were ground down to a single layer of channels and polished. The ceramic material was washed several times with deionized water during and after grinding and polishing.

The first step in developing a high oxygen transfer system is to establish a procedure to make the walls permeable to oxygen and impermeable to the nutrient medium. The method use for these experiments using the single layer of channels as prepared above was to apply a gas permeable, liquid impermeable membrane to the polished faces of the ceramic layer. W. L. Gore and Associates, Inc., has developed a line of Gore-Tex ® membranes made of expanded polytetrafluoroethylene which are waterproof yet vapor permeable. The 0.2 micron pore size Gore-Tex ®, polypropylene scrim laminate was used in these experiments. The small pore size can prevent contamination of the medium by foreign microbes.

Figure 6B:
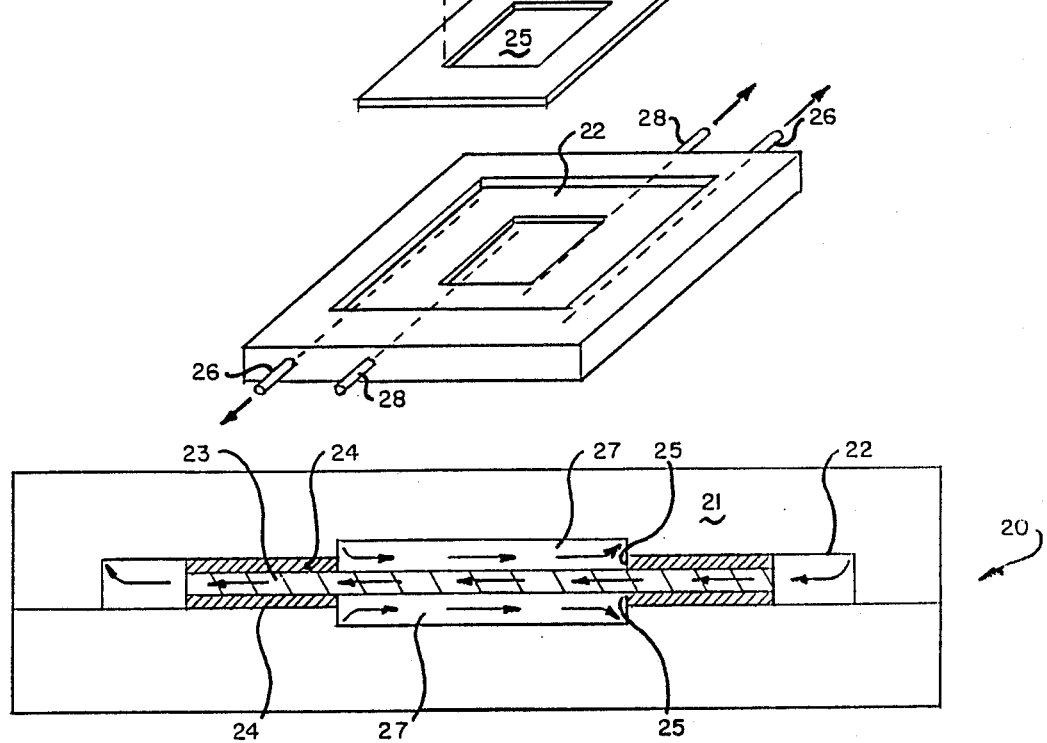
Figure 7:
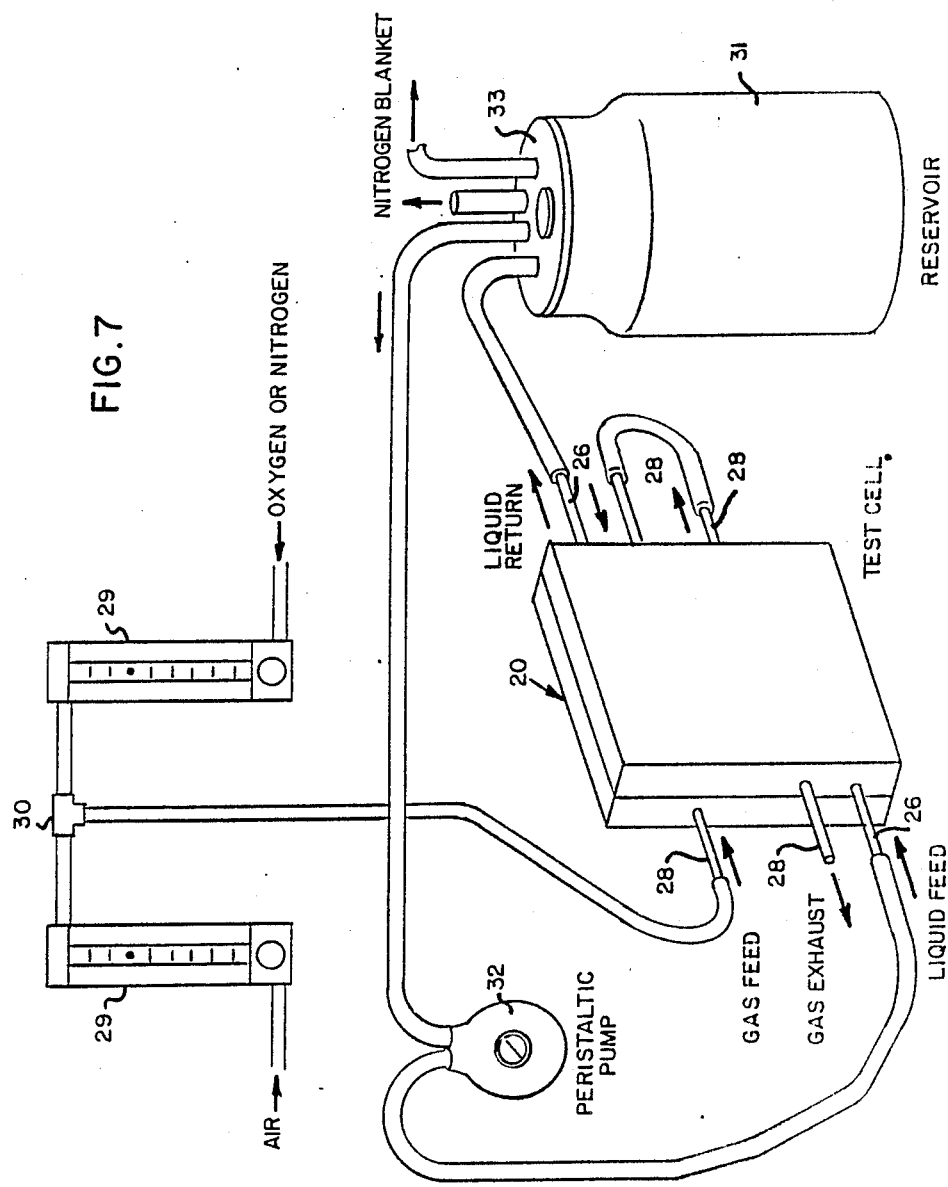
FIG. 7 is a view in perspective of a flow system for use with the test cell of FIGS. 6A and 6B.
Figure 8A:
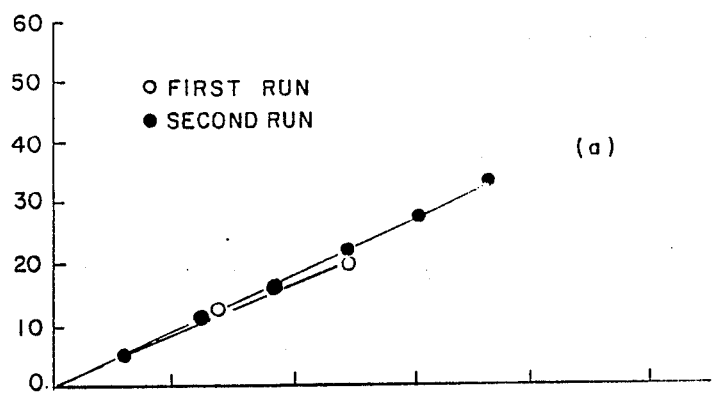
FIGS. 8A and 8B are a series of plots of experimental results for experiments performed with the test cell of FIG. 6A and 6B; and, FIGS. 9A and 9B are a series of plots of experimental results for experiments performed using low density and high density cultures respectively.
Figure 8A:
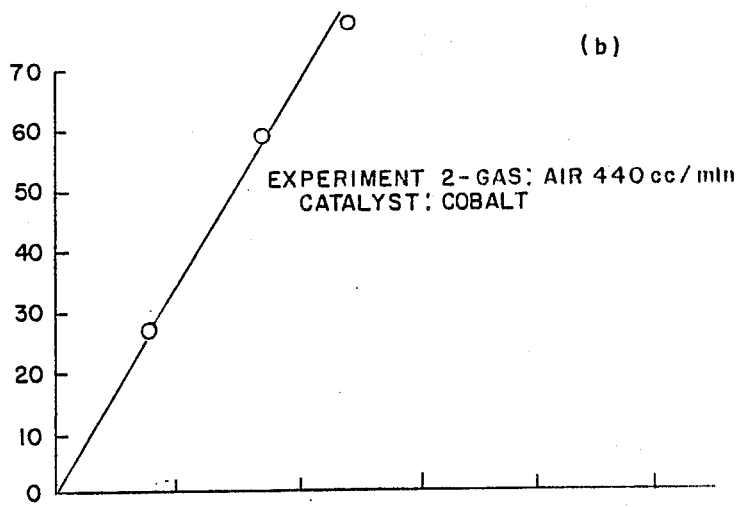
Figure 8A:
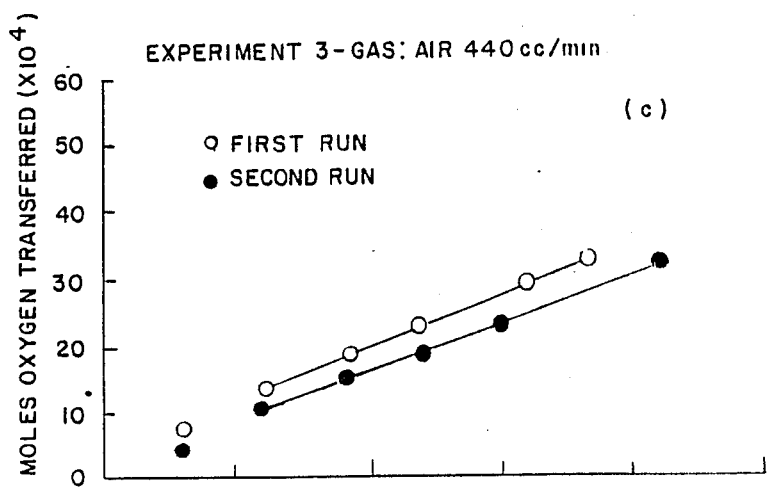
Figure 8B:
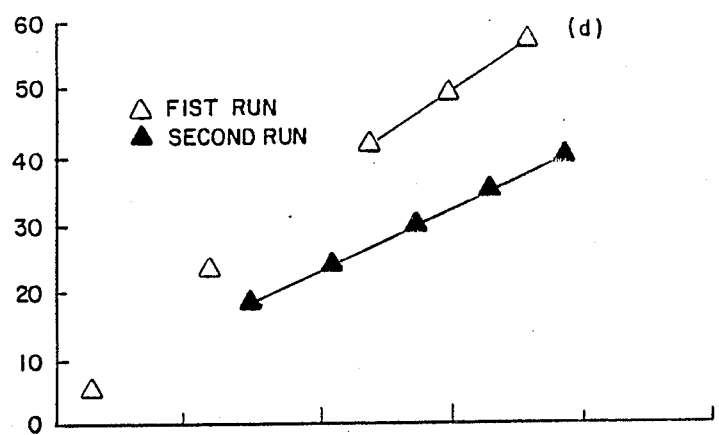
Figure 8B:
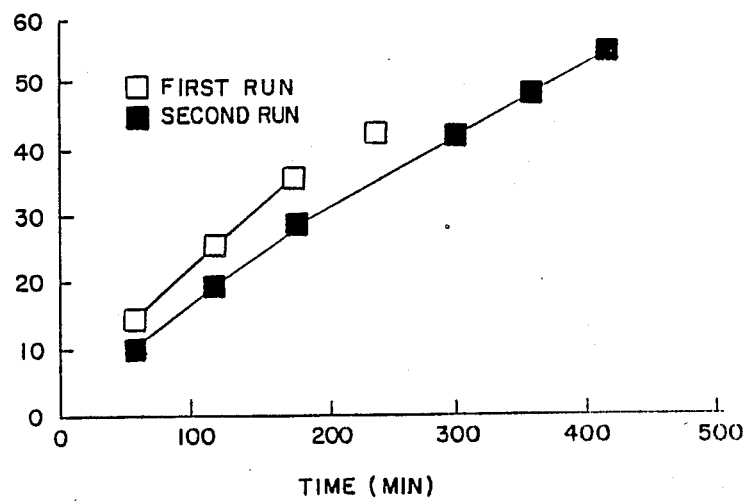

Referring now to FIGS. 6A, 6B, and 7, there is shown a test cell 20 for demonstrating the invention. One half of the cell 21 contains a well 22 into which a piece of a monolith 23, 4" by 4" by 1" layer of channels, prepared as previously described, is mounted between two silicone rubber foam gaskets 24, 4" by 4", with a 2" square opening 25. At each of this well there are flow ports 26 to allow fluid to be fed into one port 26, flow through the channels of the ceramic material 23, and exit through the other port 26 when the cell is assembled. The ceramic piece and gaskets are sandwiched in the assembled cell so that a 2" by 2" by 1/16" deep flow passage 27 is aligned with the opening in the gaskets; the fluid entrance and exit ports 28 to these passages allow fluid to be passed over both external faces of the ceramic material 23. In all of the experiments reported here, the liquid was fed through the channels of the ceramic material 23 and the gas stream was passed outside the ceramic in passage 27. Although the flow in the cell is countercurrent rather than cross-flow, the distances within the cell 20 are sufficiently small that the data will reasonably predict mass transfer behavior in a cross-flow configuration. The halves of cell 20 are milled from 6" by 7" by ¾" blocks of aluminum and are hard anodized. The gaskets and tubing used are silicone rubber.

The test cell 20 is at the center of the apparatus shown in FIG. 7. The gases are metered through Brooks Rotoflow meters 29 and mixed in a mixing tee 30. The gas is circulated over the external faces of the ceramic piece in the cell 20, i.e. through the ports designated 28 as in FIGS. 6A, first through one-half of the test cell, then the other, then exhausted to the atmosphere as shown in FIG. 7. The bulk of the sulfite solution is in the reservior 31 is stirred and kept under a nitrogen blanket by continuous flushing with nitrogen to prevent air oxidation. The solution is recirculated by a peristaltic pump 32 through the channels of the ceramic mounted in the test cell, i.e. through the ports 26. The gas and liquid streams run countercurrent with respect to one another. Samples of the sulfite solution are pipetted from the reservoir 31 through a port in its lid 33.

The rate of oxygen consumption was measured by determination of the unoxidized sulfite-ion content of the solution, sampled at intervals during each run. Duplicate 10 ml samples were taken using nitrogen flushed pipettes. Each sample was run immediately into an excess (20 ml) of freshly pipetted standard (0.1N) iodine reagent, the tip of the pipette being slightly submerged in the iodine solution, in a glass stoppered 250 ml erlenmeyer flask. The flasks were swirled and allowed to react for 10 minutes for 20 minutes before analysis by back titration with 0.01N standard thiosulfate solution to a starch indicator endpoint.

A series of experimental examples using Gore-Tex ® 0.2 μm pore size polypropylene laminate membranes as the perm-selective barrier on the ceramic were conducted. The oxygen transfer rates from gas to liquid as determined by sulfite oxidation range were from 1.8 to 6.6 g $O_2$ per, total reactor volume per hour. The data, presented as plots of moles of oxygen transferred, measured by iodometric titration, versus time, are shown in FIG. 8.

EXAMPLE 1

A mixture of 1 volume air to 1 volume nitrogen in the gas stream was used. The total gas flow rate was 440 cc/min, and the total liquid flow rate was 95 cc/min. The liquid was a 0.1M sodium sulfite solution, $10^{-4}$M in copper ion, added as $CuSO_4.5H_2O$. The solution was adjusted to pH 8, and the pH was controlled to $+0.02$ pH units by addition of 1M NaOH during each run. The slope of the line shown through the data for the first run is $8.34 \times 10^{-6}$ moles $O_2$ min$^{-1}$; for the second run it is $8.95 \times 10^{-6}$ moles $O_2$ min$^{-1}$. Since the test cell simulates a section 2" by 2" by 1 layer of a cross-flow monolith, which is $7.57 \times 10^{-3}$ l in volume for the monoliths used in this study, these oxygen transfer rates on a per volume basis are 2.12 and 2.27 g $O_2$l$^{-1}$hr$^{-1}$, respectively.

EXAMPLE 2

Air was used as the gas, again at gas and liquid flow rates of 440 and 95 cc/min, respectively. The liquid solution was a 0.1M sodium sulfite solution, $10^{-4}$ in cobalt ion added as $CoSO_4 \cdot 7H_2O$). The solution was adjusted to pH 8, and controlled to $+0.02$ pH units throughout the experiment. The slope of the line through the data is $2.609 \times 10^{-5}$ moles min$^{-1}$, corresponding to $O_2$ transfer rate of 6.62 g $O_2$l$^{-1}$hr$^{-1}$.

EXAMPLE 3

Air was used as the gas with a gas flow rate of 440 cc/min and a liquid flow rate of 95 cc/min. The liquid was 0.1M $SO_3$ with $10^{-4}$M copper ion, with no pH control. The shape of the curves through the data points, showing an oxygen consumption rate decreasing with time, is probably due to a pH effect: initially the solution is basic, around pH 12; the reaction is known to liberate hydrogen ions, so the basic pH drives the reaction forward more rapidly; the effect decreases as the pH decreases. The later points fall on lines corresponding to $7.76 \times 10^{-6}$ and $7.16 \times 10^{-6}$ moles $O_2$·min$^{-1}$, or 1.97 and 1.82 g $O_2$·l$^{-1}$hr$^{-1}$, for the first and second runs, respectively. This value is much lower than the results using cobalt ions as the catalyst in Example 2, although the gas and flow rates are the same. This is largely due to the fact that cobalt is a faster catalyst for sulfite oxidation, resulting in a greater dissolved oxygen gradient.

EXAMPLE 4

A mixture of 1 volume air: 1 volume oxygen as the gas was used with a gas flow rate of 440 cc/min, a liquid flow rate of 95 cc/min. As in Example 3, the liquid was 0.1M $SO_3$ with $10^{-4}$ copper ion, with no pH control. Again the data show a decrease in oxygen absorption rate over the first few hours. The later points of each run fall nicely on lines with slopes $12.89 \times 10^{-6}$ and $9.18 \times 10^{-6}$ moles $O_2$.min$^{-1}$ for the first and second runs respectively. These correspond to oxygen transfer rates of 3.27 and 2.33 g $O_2$·l$^{-1}$hr$^{-1}$. It is worth noting that these values differ considerably from triple the values for Example 3 although the only difference in the experimental conditions is tripling the $O_2$ concentration in the gas stream. This demonstrates the fact that a kl a type of correlation for this reactor configuration is inappropriate.

EXAMPLE 5

This experiment was conducted using 1 volume air: 1 volume oxygen, as in Example 4, but with a higher gas flow rate of 660 cc/min. The liquid and liquid flow rate were the same as in Example 4. Again the oxygen consumption rate decreases with time. In the first run, from hours 1 to 4 a slope of $17.31 \times 10^{-6}$ moles $O_2$·min$^{-1}$, or 4.62 g $O_2 \cdot l^{-1}$ was observed. The second run was broken into two intervals: from 1 to 3 hours, with $14.95 \times 10^{-6}$ moles $O_2$·min$^{-1}$, or 3.79 g $O_2 \cdot l^{-1}$ and from 3 to 7 hours, with $10.93 \times 10^{-6}$ moles $O_2$·min$^{-1}$, or 2.77 g $O_2 \cdot l^{-1}$hr$^{-1}$. Comparing these with the values for Example 4, it is evident that increasing the gas flow rate increases oxygen transfer in this range of gas flow rate and oxygen consumption.

The economic evaluation of a fermentation process depends on the power dissipated in the reactor. Oxygen-transfer performance in particular can be associated with an oxygen-transfer efficiency as kg $O_2$/l·hr oxygenation per kW/l power dissipated in order to achieve that oxygenation rate. The reactor volume in the test cell was too small to measure the power dissipated. However, it is possible to estimate the frictional losses in a cross-flow monolith for the flow rates used in these experiments.

The largest Reynolds number in either the gas or liquid flows in any experiment was below 40. The power requirement was estimated by approximating the channels as cylinders with the same hydraulic radius. The kinetic drag can be correlated as $$F_D = f \cdot A^* \cdot KE^*$$

where $A^*$ is the wetted surface area, $KE^*$ is the average kinetic energy per unit volume ($1/2\rho v^2$, with density $\rho$ and fluid velocity v) and f is the friction factor, (64/Re, for laminar flow in tubes). From the drag, the power per unit volume, neglecting end effects, can be calculated as $$P/V = F_D \cdot v$$

The power required for the liquid and gas streams was calculated for a 10 cm edge cube to arrive at the power per 1 reactor volume given in Table 1 as follows:

TABLE 1

| Example | Power Requirement (W/l) | Oxygen Transfer Rate (g $O_2$/l hr) | Oxygenation Efficiency (kg $O_2$/kW hr) |
|---|---|---|---|
| 1 | $3.6 \times 10^{-3}$ | 2.12 | 588 |
|   |   | 2.27 | 631 |
| 2 | $3.6 \times 10^{-3}$ | 6.62 | 1840 |
| 3 | $3.6 \times 10^{-3}$ | 1.97 | 550 |
|   |   | 1.82 | 508 |
| 4 | $3.6 \times 10^{-3}$ | 3.27 | 914 |
|   |   | 2.33 | 651 |
| 5 | $4.2 \times 10^{-3}$ | 4.62 | 1102 |
|   |   | 3.79 | 905 |
|   |   | 2.77 | 662 |

As shown in the foregoing specific examples, oxygen transfer rates of 1.8 to 6.6 g per liter total volume per hour, roughly equal to 3.6 to 13.2 g per liter liquid volume per hour, were observed for the experimental analogue to the cross-flow reactor using Gore-Tex ® 0.2 μm pore size polypropylene scrim laminate membrane. These transfer rates equal and surpass the maximum aeration rates observed in stirred tanks. One of the highest oxygen demands observed in a stirred tank is 260 mmol $O_2^{-1}h^{-1}$ for *Azotobacter vinelandii*. This is equal to 8.3 g $O_2 l^{-1}h^{-1}$, well within the range of transfer rates per liter liquid volume observed using a sulfite system. This does not guarantee that this transfer rate will be obtained when immobilized cells are used, since the gap between the membrane gas-liquid interface and the biofilm (FIG. 4) and the diffusivity of oxygen in the biofilm might reduce the effective driving force or increase the barrier to oxygen transport, respectively. It does indicate, however, that the membrane-ceramic composite can sustain the required oxygen flux. Another basis for comparison is the number of cells per liter which can be supported in the biofilm given this range of oxygen transfer rates. Assuming that oxygen is the limiting substrate and allowing a very high oxygen requirement per cell of $5 \times 10^{-12}$ g $O_2$ per cell per hour, the observed oxygen transfer rates could support a population density ranging from $3 \times 10^{11}$ to $13 \times 10^{11}$ cells per liter reactor volume, or $6 \times 10^{11}$ to $26 \times 10^{11}$ cells per liter liquid volume. Compared to $10^9$ cells per liter liquid for suspended cultures this represents an improvement of roughly two orders of magnitude.

The power requirements for a cross-flow monolithic reactor consists in the power required to maintain the pressure drops to drive the gas and liquid flows through the channels. Since no liquid agitation is required and since the channels are unhindered, this power requirement is expected to be much lower than that for a stirred tank or packed column. Using an approximate method to estimate the power requirement for a cross-flow monolith operating with the same superficial gas and liquid velocities as used in the experiments, values of the oxygenation efficiency were estimated for the examples presented in Table 1. The oxygenation efficiencies range roughly from 500 to 1000 kg $O_2$ per kW·hr. For the sake of comparison the values tabulated by Serieys, et al, *Biotechnology and Bioengineering*, XX, pp. 1393-1406 (1978), from the work of various researchers on gas-liquid contactors range from 0.3 to 7.5 kg $O_2$ kW·hr. While a precise value of the oxygenation efficiency for a cross-flow monolithic reactor cannot be predicted, this comparison indicates that it is likely to be orders of magnitude better than conventional reactors.

The results of the experimental studies reported in the previous section show that should an overall volumetric mass transfer coefficient (k a) be calculated on the basis of the obtained oxygen transfer rates, this coefficient would depend on the oxygen concentration in the gas phase, the kinetics of the reaction, and the gas flow rate. The detected trends are correct, i.e. the coefficient increases with the gas-phase $O_2$ concentration, gas flow rate and velocity of reaction, but cannot be quantitatively predicted by using the simple models usually employed for the description of k la in agitated vessels with outside aeration. This is not surprising because several ill-defined processes participate in the transport of oxygen through the membrane-ceramic composite material.

EXAMPLE 6

Murine-murine hybridoma cells, CRL-1606, which produce an IgG monoclonal antibody to human fibronectin were obtained from the American Type Culture Collection (ATCC, Rockville, Md.). The cells were thawed rapidly and passaged as necessary in DMEM (Mediatech, Washington, D.C.) supplemented with 5% FBS (Sigma Chemical, St. Louis, Mo.) for an unspecified period of time. All media used were supplemented with 100 U/mL penicillin and 100 $\mu$g/mL streptomycin (Mediatech, Washington, D.C.).

Cordierite ceramic monoliths, 200 cells/in$^2$, were provided by Corning Glass Works (Corning, N.Y.) in cylinders four inches long. These monoliths were sectioned into slabs 4"×4"×three layers. The slabs were immersed in a boiling solution of 10% nitric acid for one hour to precipitate any heavy metals ions which may have been introduced during the manufacture of the monoliths. The ceramics were washed extensively with de-ionized water and autoclaved in calcium- and magnesium-free phosphate buffered saline (PBS) to allow the pH to return to neutral. The slabs were sliced and polished to produce one single-layer slab and one double-layer slab.

In order to separate the medium from the contacting gas stream, the ceramic slab was sandwiched between two vapor permeable, liquid impermeable Gore-Tex ® membranes provided by W. L. Gore and Associates (Elkton, Md.). The polypropylene scrim laminate membrane had a 0.2 pore size with a total porosity of 78%.

The ceramic slabs were sandwiched between two membranes in an anodized aluminum block using silicone rubber gaskets. A gas stream consisting of 10% $CO_2$ in air at a total flow rate of 30 cc/min contacted the medium stream across each membrane through a 2" square "window" cut from the rubber gaskets. Medium flowed through the ceramic monolith in a direction counter-current to the gas stream at an average channel velocity of 4.2 cm/min. Since single pass conversion was so low, medium recirculated continuously using a medium reservoir external to the monolith. Medium was replaced every three days or when the pH had dropped sufficiently by draining all lines and aspirating spent medium from the reservoir. The reservoir, monolith bioreactor, and all associated pumps and tubing were placed in a humidified, 10% $CO_2$ incubator. Indirect measurement of immobilized cell number was achieved by collecting samples of medium every eight to twelve hours and assaying the samples for glucose, lactate, and monoclonal antibody.

Two experiments demonstrating the feasibility of culturing hybridoma cells in a ceramic matrix with Gore-Tex ® membranes are presented below. The first experiment consisted of a double-layer, 4"×4" ceramic slab in which cells were inoculated at a low density. The second experiment consisted of a single-layer, 4"×4" slab in which cells were inoculated at a much higher density.

Figure 9A:
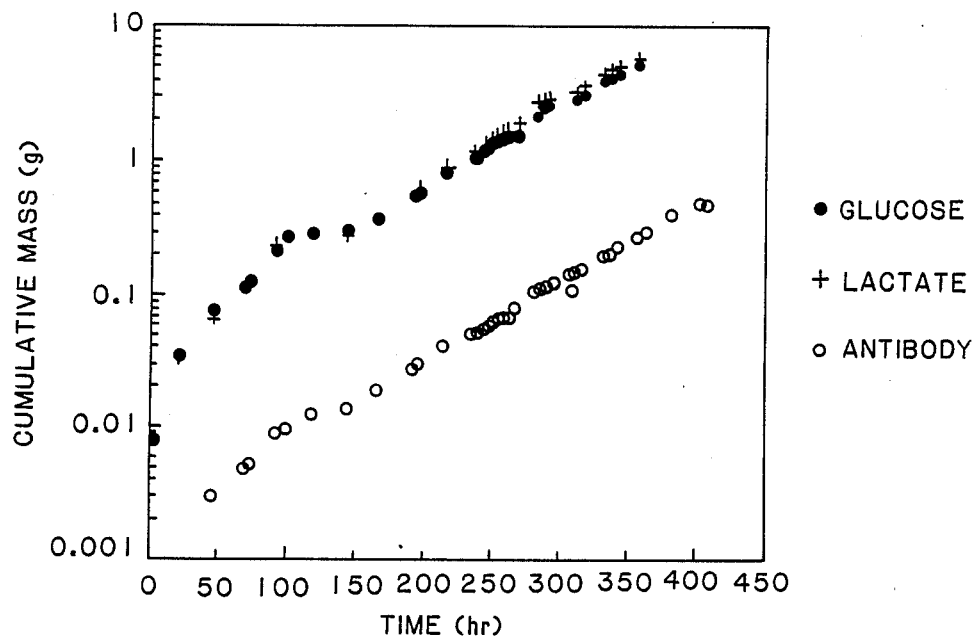

Cumulative glucose consumption and cumulative lactate and monoclonal antibody production is shown in FIG. 9A for the first experiment. The bioreactor was inoculated with $2.0 \times 10^7$ cells as determined by hemacytometer cell counts. This corresponds to an average cell density of $1.2 \times 10^6$ cells/cm$^3$ wall.

If cell growth is exponential and specific rates of consumption and production are constant, then total substrate consumption or product accumulation can be related to the growth rate. A non-linear least squares fit of the data gives a value for the growth rate of 0.013 hr$^{-1}$±2% for the culture, a value somewhat lower than in batch cultures but still reasonable. Based on this estimate, the average cell density at the end of the experiment was approximately $1.2 \times 10^8$ cells/cm$^3$ wall.

Figure 9B:
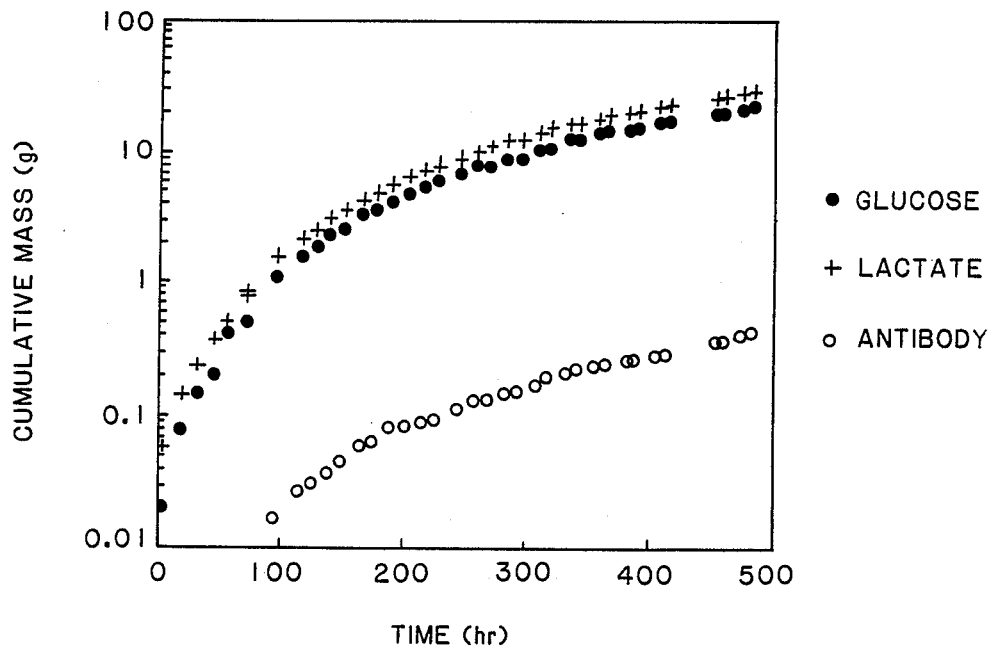

In the second experiment the monolith was inoculated with $2.4 \times 10^8$ cells, corresponding to an average density of $2.5 \times 10^7$ cells/cm$^3$ wall. As shown in FIG. 9B the exponential growth phase occurs only in the first 100 hours, followed by a gradual decline in grown rate as the culture reaches what appears to be a state of confluency. After about 250 hours, the bioreactor produces monoclonal antibody at a constant rate of 1.2 mg/hr. Since the cell line continues to secrete antibody, oxygen must be supplied to these cells at sufficient levels to maintain viability and antibody productivity.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description; and all changes which come within the meaning and range of equivalency of the claims are therefore intended to be embraced therein.

What is claimed is:

1. An apparatus for carrying out transfer and separation of fluid products from biological reactions comprising:
   (a) a unitary structure formed of ceramic material having a plurality of flow passages therein including first and second sets of said flow passages and arranged so that individual passages of said first set of passages are adjacent to individual passages of said second set of passages being separated by walls formed of said ceramic material, said ceramic material being porous to provide selective mass transfer of oxygen and biological reaction products while containing liquid in said second set of passages;
   (b) a first fluid means for providing fluid communication with said first set of flow passages and a first fluid outlet means for removing fluid from said flow passages;
   (c) a second fluid communication means providing fluid communication with said second set of said flow passages and a second fluid outlet means for removing fluid from said flow passages; and
   (d) means connected to said first fluid communication means for establishing flow of a fluid which will yield gaseous oxygen through said first set of flow passages and means connected to said second set of flow passages for establishing fluid flow through said second set of flow passages whereby a gaseous oxygen flow producing gradient through said porous ceramic material will be established between said first and second sets of passages.

2. An apparatus according to claim 1 wherein the passages of said first and said second sets of flow passages are linear and mutually parallel to the other passages of said first and said second sets respectively.

3. An apparatus according to claim 2 wherein said first and second sets of flow passages respectively are mutually parallel.

4. An apparatus according to claim 2 wherein said first and second sets of flow passages are mutually oblique.

5. An apparatus according to claim 2 wherein said first and second sets of flow passages are mutually perpendicular.

6. An apparatus according to claim 1 further comprising a gaseous oxygen permeable membrane covering walls of said first or second set of passages.

7. An apparatus according to claim 6 wherein said membrane covers inside walls of said first set of passages.

8. An apparatus according to claim 6 wherein said membrane covers inside walls of said second set of passages.

9. An apparatus according to claim 1 further comprising a coating on inside walls of the second set of passages, said coating comprising a compound adapted to attach to said ceramic material, said coating being further adapted to immobilize biological reaction materials coming into contact therewith.

10. An apparatus according to claim 6 wherein said membrane is liquid impermeable.

11. An apparatus according to claim 6 wherein said membrane will permit passage of selected biological reaction products.

12. An apparatus according to claim 1 wherein cells are immobilized on inside walls of the second set of flow passages.

13. A method for carrying out oxygen transfer useful in biological reactions comprising:
   (a) providing a unitary structure formed of ceramic material having a plurality of flow passages therein including first and second sets of said flow passages which are adapted to be in fluid communication with different fluid sources and wherein individual passages of said first set of passages are adjacent individual passages of said second set of passages being separated therefrom by walls formed of said ceramic material, said ceramic material being porous to provide selective mass transfer of gaseous oxygen and biological reaction products from said first set of passages while retaining liquid in said second set of passages;
   (b) contacting said first set of flow passages with a fluid will yield gaseous oxygen through said first set of flow passages; and
   (c) establishing fluid flow through said second set of flow passages whereby an oxygen flow producing gradient will be established through said porous ceramic material between said first and second sets of passages.

14. A method according to claim 13 further comprising applying a gaseous oxygen permeable membrane to cover inside walls of either said first or second sets of passages prior to contacting said passages with said oxygen yielding fluid.

15. A method according to claim 14 wherein said membrane is applied to the inside walls of said first set of passages.

16. A method according to claim 14 wherein said membrane is applied to the inside walls of said second set of passages.

17. A method according to claim 13 further comprising applying a coating to inside walls of the first set of passages; said coating comprising a compound adapted to attach to said ceramic material, said coating being further adapted to immobilize biological reaction materials coming into contact therewith.

18. A method according to claim 13 wherein cells are immobilized on inside walls of the second set of flow passages.

* * * * *